United States Patent
Sauer et al.

(10) Patent No.: US 6,908,458 B1
(45) Date of Patent: Jun. 21, 2005

(54) SWELLABLE STRUCTURE HAVING A PLEATED COVER MATERIAL

(75) Inventors: Barbara O. Sauer, Fremont, WI (US); Laura Turner, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 222 days.

(21) Appl. No.: 09/648,427

(22) Filed: Aug. 25, 2000

(51) Int. Cl.$^7$ .............................................. A61F 13/15
(52) U.S. Cl. ............................ 604/385.16; 604/385.01
(58) Field of Search ...................... 604/385.12, 385.16, 604/385.01, 367

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,763 A | 3/1970 | Hartmann |
| 3,542,615 A | 11/1970 | Dobo et al. |
| 3,692,618 A | 9/1972 | Dorschner et al. |
| 3,776,233 A | 12/1973 | Schaar |
| 3,802,817 A | 4/1974 | Matsuki et al. |
| 3,849,241 A | 11/1974 | Butin et al. |
| 4,340,563 A | 7/1982 | Appel et al. |
| 4,787,896 A | 11/1988 | Houghton et al. |
| 4,790,839 A | 12/1988 | Ahr |
| 5,057,368 A | 10/1991 | Largman et al. |
| 5,069,970 A | 12/1991 | Largman et al. |
| 5,171,236 A | 12/1992 | Dreier et al. |
| 5,277,976 A | 1/1994 | Hogle et al. |
| 5,306,266 A | 4/1994 | Freeland |
| 5,368,926 A * | 11/1994 | Thompson et al. ......... 428/913 |
| 5,466,410 A | 11/1995 | Hills |
| 5,520,674 A | 5/1996 | Lavon et al. |
| 5,776,122 A * | 7/1998 | Faulks et al. ............. 604/385.2 |
| 5,797,892 A * | 8/1998 | Glaug et al. ................ 604/291 |
| 5,895,382 A | 4/1999 | Popp et al. |
| 6,022,338 A * | 2/2000 | Putzer ..................... 604/385.1 |
| 6,224,961 B1 * | 5/2001 | Hsueh et al. ............... 428/220 |
| 6,264,641 B1 * | 7/2001 | Van Gompel et al. ...... 604/378 |
| 6,293,935 B1 * | 9/2001 | Kimura et al. ............. 604/378 |
| 6,312,416 B1 * | 11/2001 | Brisebois et al. ........... 604/358 |
| 6,423,045 B1 * | 7/2002 | Wise et al. ................ 604/379 |
| 6,595,972 B1 * | 7/2003 | Wise et al. ............ 604/385.01 |

* cited by examiner

*Primary Examiner*—Larry I. Schwartz
*Assistant Examiner*—C. Lynne Anderson
(74) *Attorney, Agent, or Firm*—Pauley Petersen & Erickson

(57) ABSTRACT

A personal care absorbent article, such as an infant diaper, a training pant, an incontinence garment and the like, having at least one swellable structure attached thereto for use as a containment dam or support structure. The swellable structure having a swellable layer and a cover material adapted to expand upon swelling of the swellable layer. The pleated cover material allows the swellable layer to swell freely in a z-direction.

25 Claims, 4 Drawing Sheets

SWELLABLE STRUCTURE HAVING A PLEATED COVER MATERIAL

BACKGROUND OF THE INVENTION

1. Field of the Invention

This invention relates to a personal care absorbent article, such as an infant diaper, a training pant, an incontinence garment and the like, having a swellable structure attached thereto for use as a containment dam or support structure to contain and manage body exudates. More particularly, this invention relates to a swellable layer which swells in a z-direction, and a pleated cover material adapted to expand upon swelling of the swellable layer to allow the swellable layer to freely swell.

2. Description of Prior Art

Conventional personal care absorbent articles may have expandable structures or elements for containment and management of body exudates. For example, conventional personal care absorbent articles may have an expandable structure which provides void space for fecal containment and management. Such expandable structures may also provide displacement of a topsheet relative to a backsheet of the article.

These structures typically have poor component integrity, for example superabsorbent (SAM) migration of a SAM/fluffbatt. These structures expand in an uncontrolled manner as fluid is absorbed, for example the structures may expand in undesirable directions. Further, these structures have a wet, rough feel which does not offer good surface aesthetics. One solution to these problems is to provide a cover material to maintain the component integrity and provide a soft, dry surface. Accordingly, the cover material must be expandable to accommodate the expansion of the structure during article use.

It is apparent that there is a need for a cover material that allows the underlying structure to freely expand in a controlled manner, while providing a soft, dry, aesthetically pleasing surface.

SUMMARY OF THE INVENTION

In response to the discussed difficulties and problems encountered in the prior art, a personal care absorbent article, for example a disposable diaper, having at least one swellable structure attached thereto for use as a containment dam and/or support structure, has been discovered.

The swellable structure has a swellable layer which is swellable from a temporary compressed configuration having an initial thickness to a swelled configuration having a final thickness greater than the initial thickness. Desirably, the swellable layer is swellable in only one direction, for example in the z-direction.

The swellable layer can be activated to swell upon the absorption of a fluid, such as urine, the application of heat to the swellable layer and/or the introduction or presence of an activating chemical component.

Upon activation of the swellable layer, the temporary bonds formed to hold the swellable layer in a compressed configuration are broken and the swellable layer opens or swells to the swelled configuration. In the swelled configuration, the swellable structure is effective in creating a containment dam and/or a support structure to manage and contain body exudates.

The swellable layer can be any structure which is generally compressible, conformable, non-irrating to the wearer's skin, and desirably capable of absorbing and retaining liquids and certain body exudates, for example SAM/fluff batts, compressed cellulose, foam structures, and the like. The swellable layer may have a generally rectangular shape, a semi-circular shape, a arcuate shape or an angular or tapered shape which conforms to the wearer's body.

A cover material covers at least a portion of the swellable layer and is adapted to expand upon swelling of the swellable layer. In one embodiment, the cover material has a pleat configuration for accommodating the swellable layer. For example, the pleat configuration may be a single z-fold pleat, a multiple accordion pleat or a gusset pleat. The cover material which contacts the skin of the wearer while the diaper is worn and prevents substantial contact of the swellable layer with the skin of the wearer, has soft drape characteristics and good fluid penetration properties while maintaining a dry feel and cloth-like aesthetics.

With the introduction of a fluid, for example, the absorbent swellable layer swells as it absorbs the surrounding fluid. As the surrounding fluid is absorbed, the thickness of the absorbent swellable layer in the z-direction increases. The pleat configuration of the cover material allows the absorbent swellable layer to continue to absorb the surrounding fluid and increase in thickness until it reaches a maximum swelled thickness, without interference from the cover material.

With the foregoing in mind, it is a feature and advantage of this invention to provide a swellable structure having a swellable layer which is swellable in the z-direction to provide containment dams or support structures for containment and management of body exudates.

It is also a feature and advantage of this invention to provide a pleated cover material which is adapted to expand to accommodate swelling of the swellable layer during article use and prevent the swellable layer from swelling in undesired directions.

BRIEF DESCRIPTION OF THE DRAWINGS

These and other objects and features of this invention will be better understood from the following detailed description taken in conjunction with the drawings wherein.

DEFINITIONS

Figure 1:
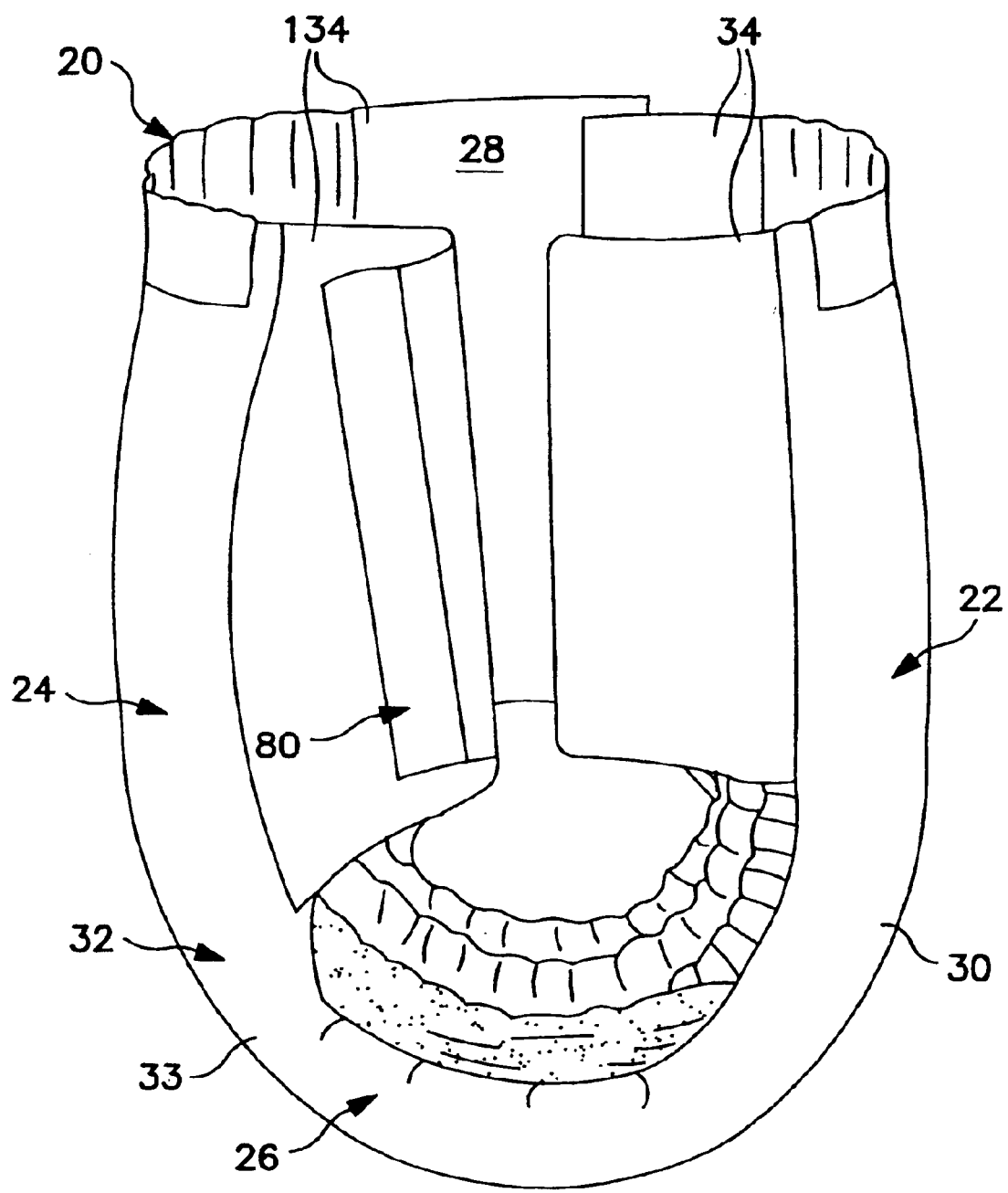
FIG. 1 is a representative perspective view of a child's training pant in a partially fastened position, in accordance with one embodiment of this invention.

As used herein, "longitudinal", "transverse" and "lateral" have their customary meaning. The longitudinal axis lies in the plane of the article and is generally parallel to a vertical plane that bisects a standing wearer into left and right body halves when the article is worn. The transverse or lateral axis lies in the plane of the article generally perpendicular to the longitudinal axis. The article as illustrated in FIG. 1 is longer in the longitudinal direction than in the transverse direction. The term "z-direction" refers to a direction generally perpendicular to the longitudinal direction and the transverse direction.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" also includes all possible geometric configurations of the molecule. These configurations include, but are not limited to, isotactic, atactic, syndiotactic and random symmetries.

As used herein, the term "nonwoven" or "nonwoven web" means a structure of individual fibers or threads which are interlaid, but not in an identifiable repeating manner. Nonwoven webs have been, in the past, formed by a variety of processes such as, for example, meltblowing processes, spunbonding processes, coforming processes, hydroentangling, air-laid and bonded carded web processes.

As used herein, the term "spunbond fibers" refers to small diameter fibers which are formed by extruding molten thermoplastic material as filaments from a plurality of fine, usually circular capillaries of a spinneret, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, and U.S. Pat. No. 3,542,615 to Dobo et al. Spunbond fibers are generally not tacky when they are deposited onto a collecting surface. Spunbond fibers are generally continuous and have average diameters (from a sample of at least 10 fibers) larger than 7 microns, more particularly, between about 10 and 30 microns. The fibers may also have shapes such as those described in U.S. Pat. No. 5,277,976 to Hogle et al., U.S. Pat. No. 5,466,410 to Hills, and U.S. Pat. No. 5,069,970 and U.S. Pat. 5,057,368 to Largman et al., which describe hybrids with unconventional shapes. A nonwoven web of spunbond fibers produced by melt spinning is referred to as a "spunbond".

As used herein, the term "meltblown fibers" means fibers formed by extruding a molten thermoplastic material through a plurality of fine, usually circular, die capillaries as molten threads or filaments into converging high velocity, usually hot, gas (for example, air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, by U.S. Pat. No. 3,849,241 to Butin et al. Meltblown fibers are microfibers which may be continuous or discontinuous, are generally smaller than 10 microns in average diameter.

As used herein, the term "bonded carded web" refers to webs made from staple fibers which are sent through a combing or carding unit, which breaks apart and aligns the staple fibers in the machine direction to form a generally machine direction-oriented fibrous nonwoven web. Such fibers are usually purchased in bales which are placed in a picker or fiberizer which separates the fibers prior to the carding unit. Once the web is formed, it is then bonded by one or more of several known bonding methods.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

As used herein, the term "personal care article" or "personal care absorbent article" means feminine hygiene products, diapers, training pants, absorbent underpants, adult incontinence products and wound care products, including bandages.

These terms may be defined with additional language in the remaining portions of the specification.

DETAILED DESCRIPTION OF THE PRESENTLY PREFERRED EMBODIMENTS

The principles of the present invention can be incorporated into any suitable disposable personal care absorbent article. Examples of such suitable articles include infant diapers, training pants, feminine hygiene products, incontinence products, other personal care or health care garments, and the like. For ease of explanation, the description hereafter will be in terms of a training pant 20.

As shown in FIG. 1, a disposable absorbent article, such as a training pant 20, comprises an absorbent chassis 32 and a fastening system 80. The absorbent chassis 32 defines a front waist section or region 22, a back waist section or region 24, and a crotch section or region 26 intermediate to and interconnecting the front waist region 22 and the back waist region 24. The front waist region 22 comprises the portion of the training pant 20 which, when worn, is positioned on the front of the wearer while the back waist region 24 comprises the portion of the training pant 20 which, when worn, is positioned on the back of the wearer. The crotch region 26 of the training pant 20 comprises the portion of the training pant 20 which, when worn, is positioned between the legs of the wearer and covers the lower torso of the wearer.

The absorbent chassis 32 further comprises an inner surface 28 which is configured to contact the wearer, and an outer surface 30 opposite the inner surface 28 which is configured to contact the wearer's clothing. As show in FIG. 2, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39, as shown in FIG. 2.

Figure 2:
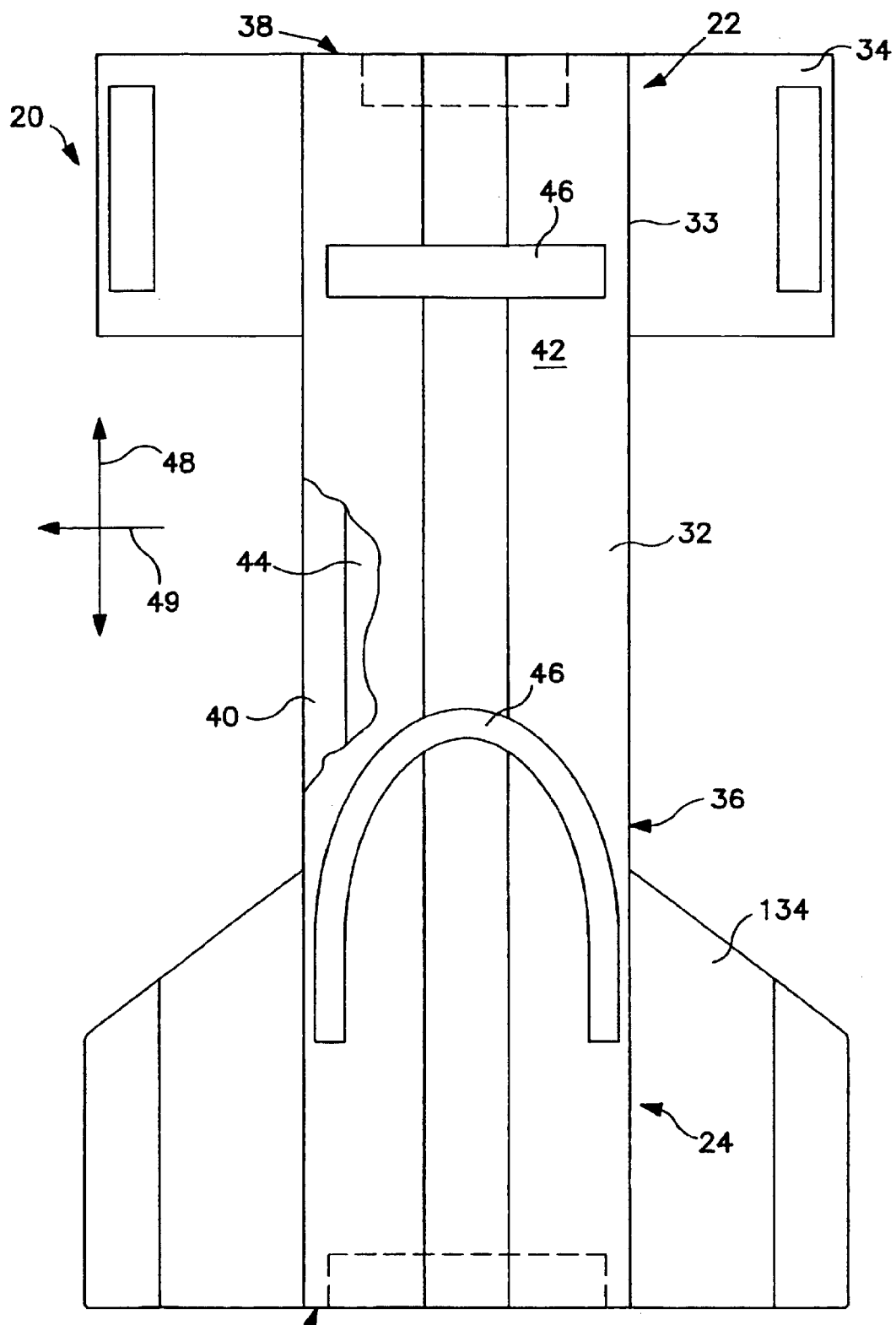
FIG. 2 is a representative plan view of a child's training pant in a flat, uncontracted state, having at least one swellable structure forming a containment dam or support structure, in accordance with one embodiment of this invention.

As shown in FIG. 2, the absorbent chassis 32 comprises a rectangular composite structure 33, a pair of transversely opposed front side panels 34, and a pair of transversely opposed back side panels 134. The composite structure 33 comprises a backsheet 40, a topsheet 42 which is connected to the backsheet 40 in a superposed relation, and an absorbent layer 44 which is located between the backsheet 40 and the topsheet 42. For reference, arrow 48 and arrow 49, depicting the orientation of the longitudinal axis and the transverse axis, respectively, of the training pant 20 are illustrated in FIG. 2.

The absorbent chassis 32 is configured to contain and/or absorb any body exudates discharged from the wearer. In accordance with one embodiment of this invention, the absorbent chassis 32 comprises at least one swellable structure 46 positioned and/or attached to the inner surface 28, as shown in FIG. 2. The swellable structure 46 can be attached to the inner surface 28 by means well known in the art, for example using an adhesive. The swellable structure 46 may be used as, for example, a containment dam or support structure to contain body exudates within one region of the training pant 20 and prevent migration and/or leakage.

In accordance with one embodiment of this invention, the swellable structure 46 comprises a swellable layer 47 and a cover material 48. Desirably, the swellable layer 47 is swellable in at least one direction, more desirably the swellable layer 47 is swellable in only one direction, for example a z-direction. Desirably, the swellable layer 47 is an absorbent swellable layer which is activated to swell upon the absorption of a fluid, such as urine. However, in accordance with other embodiments of this invention, the swellable layer 47 may be activated by other means including, but not limited to, the application of heat to the swellable layer 47 and the introduction or presence of an activating chemical component.

Figure 3:
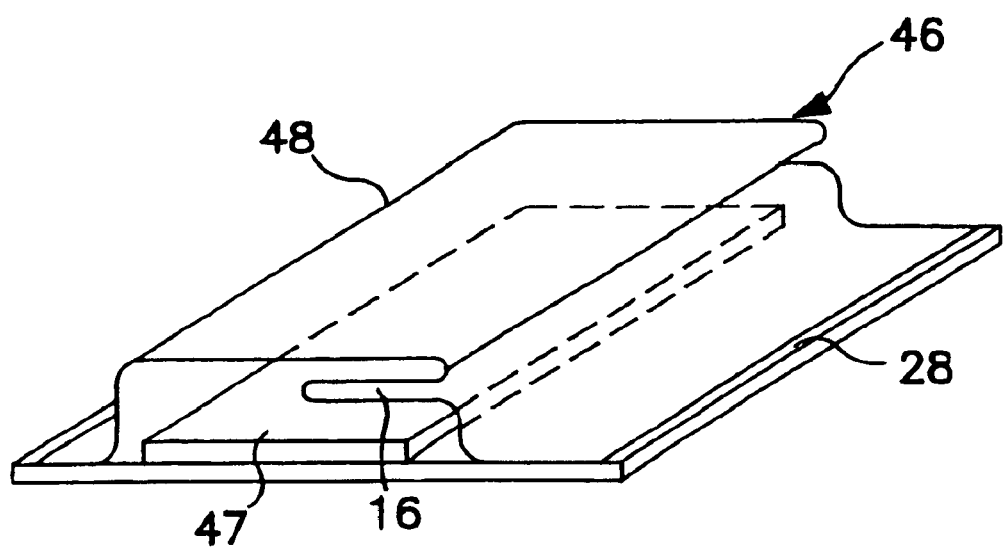
FIG. 3 is a schematic perspective view of a swellable layer in a compressed configuration and at least partially covered by a cover material having a single z-fold pleat configuration, in accordance with one embodiment of this invention.
Figure 4:
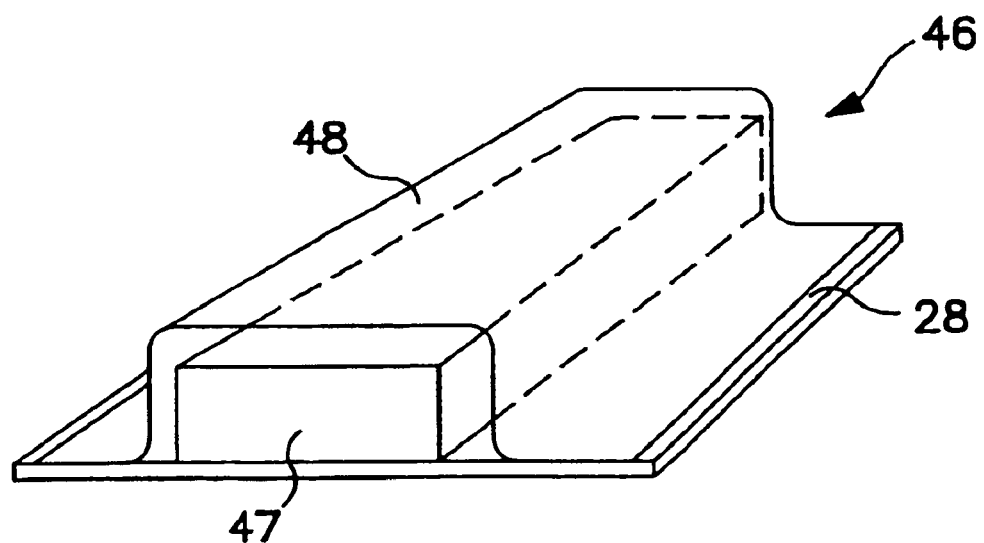
FIG. 4 is a schematic perspective view of a swellable layer in a swelled configuration and at least partially covered by a cover material, in accordance with one embodiment of this invention.

In accordance with one embodiment of this invention, the swellable layer 47 is swellable from a temporary compressed state or configuration having an initial or compressed thickness as shown in FIG. 3, to a swelled state or configuration having a final or swelled thickness greater than the initial thickness, as shown in FIG. 4. The swellable layer 47 is temporarily bonded or otherwise held in a compressed configuration by means well known in the art, for example a water-soluble adhesive. Other means known to persons having ordinary skill in the art may also be used to temporarily hold the swellable layer 47 in the compressed configuration.

Desirably, the swellable layer 47 has an initial thickness (in the z-direction) in the compressed configuration of about 0.05 inch to about 0.5 inch, more desirably about 0.1 inch to about 0.3 inch. Upon swelling, the swellable layer 47 has a desired swelled thickness (in the z-direction) in the swelled configuration of about 0.2 inch to about 1.5 inches, more desirably about 0.4 inch to about 1.0 inch.

Upon activation of the swellable layer 47, the temporary bonds formed to hold the swellable layer 47 in a compressed configuration are broken and the swellable layer 47 opens or swells to the swelled configuration. In the swelled configuration, the swellable structure 46 is effective in creating a dam and/or a support structure to manage and contain body exudates. For example, the swellable structure 46 in the swelled configuration may create a void space for containing fecal matter.

The swellable layer 47 can be any structure which is generally compressible, conformable, non-irrating to the wearer's skin, and desirably capable of absorbing and retaining liquids and certain body exudates. Desirably, but not necessarily, the swellable layer 47 comprises the same or similar material as the absorbent layer 44, discussed below.

Figure 7:
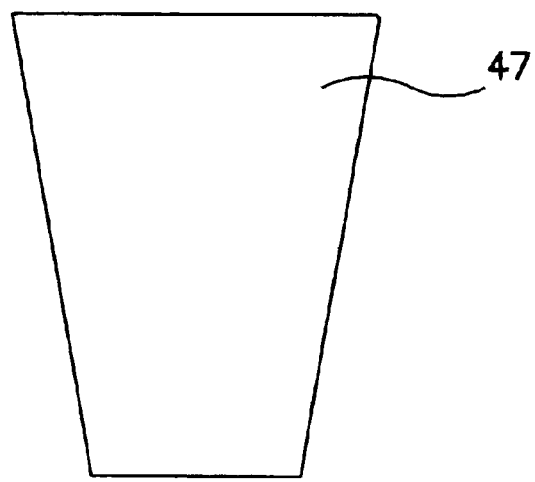
FIG. 7 is a top plan view of a swellable layer having a tapered configuration, in accordance with one embodiment of this invention.

In accordance with one embodiment of this invention, the swellable layer 47 is generally rectangular in shape, and comprises a blend of wood pulp fluff and superabsorbent material. The swellable layer 47 may have other suitable shapes, for example a semi-circular or arcuate shape, or an angular or tapered shape to better conform to the wearer's body, as show in FIG. 7.

Figure 5:
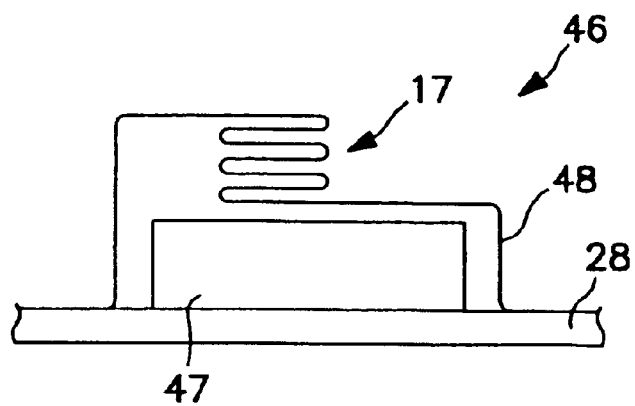
FIG. 5 is a schematic front view of a swellable layer at least partially covered by a cover material having a multiple accordion pleat configuration, in accordance with one embodiment of this invention.
Figure 6:
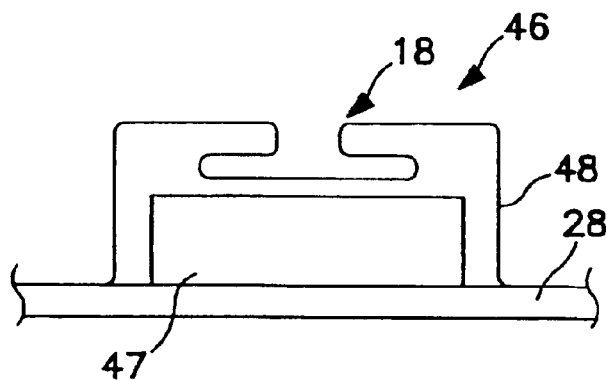
FIG. 6 is a schematic front view of a swellable layer at least partially covered by a cover material having a gusset pleat configuration, in accordance with one embodiment of this invention.

In accordance with one embodiment of this invention, the cover material 48 covers at least a portion of the swellable layer 47 and is adapted to expand upon the swelling of the swellable layer 47. The cover material 48 may be integrated with the top sheet 12 and desirably, but not necessarily, comprises a material the same or similar to the top sheet 12, as discussed below. As shown in FIG. 3, the cover material 48 has at least one pleat 16 for accommodating swelling of the swellable layer 47. Various pleat configurations may be used including, but not limited to, the single z-fold pleat 16 as shown in FIG. 3, a multiple accordion pleat 17 as shown in FIG. 5, and a gusset pleat 18 as shown in FIG. 6.

Referring to FIGS. 3 and 4, with the introduction of a fluid for example, the absorbent swellable layer 47, having an initial thickness as shown in FIG. 3, swells as it absorbs a surrounding fluid. As the surrounding fluid is absorbed, the absorbent swellable layer 47 increases in thickness in the z-direction. The pleat configuration of the cover material 48 allows the absorbent swellable layer 47 to continue to absorb the surrounding fluid and increase in thickness in the z-direction until it-reaches a maximum swelled thickness, as shown in FIG. 4, without interference from the cover material 48. Desirably, the absorbent swellable layer 47 is swellable unidirectionally, for example in the z-direction, to produce a containment dam or support structure suitable for containing and isolating body exudates within a desired region of the training pant 20. The cover material 48 generally prevents the absorbent swellable layer 47 from swelling in a longitudinal direction and/or a lateral direction. In other embodiments of this invention, the swellable layer 47 may be swellable in more than one direction.

The absorbent layer 44 can be any structure which is generally compressible, conformable, non-irritating to the wearer's skin, and capable of absorbing and retaining liquids and certain body exudates, for example SAM/fluff batts, compressed cellulose, foam structures, and the like.

In accordance with one embodiment of this invention, the absorbent layer 44 can be manufactured in a wide variety of sizes and shapes, and from a wide variety of liquid absorbent materials commonly used in the art. For example, the absorbent layer 44 can suitably comprise a matrix of hydrophilic fibers, such as a web of cellulosic fluff, mixed with particles of a high-absorbency material commonly known as superabsorbent material. In a particular embodiment, the absorbent layer 44 comprises a matrix of cellulosic fluff, such as wood pulp fluff, and superabsorbent hydrogel-forming particles. The wood pulp fluff can be exchanged with synthetic, polymeric, meltblown fibers or with a combination of meltblown fiber and natural fibers. The superabsorbent particles can be substantially homogeneously mixed with the hydrophilic fibers or can be nonuniformally mixed. The fluff and superabsorbent particles can also be selectively placed into desired zones of the absorbent layer 44 to better contain and absorb body exudates. The concentration of the superabsorbent particles can also vary through the thickness of the absorbent layer 44. Alternatively, the absorbent layer 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefild, Federal Republic of Germany. Typically, a superabsorbent material is capable of absorbing at least 15 times its weight in water, and desirably is capable of absorbing more than 30 times its weight in water.

In one embodiment, the absorbent layer 44 is generally rectangular in shape, and comprises a blend of wood pulp fluff and superabsorbent material. The absorbent layer 44 may have other suitable shapes. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent layer 44 in an amount of from about 5 to about 90 weight percent based on a total weight of the absorbent layer 44. The absorbent layer 44 suitably has a density within the range of about 0.10 to about 0.35 grams per cubic centimeter. The absorbent layer 44 may or may not be wrapped or encompassed by a suitable tissue wrap to maintain the integrity and/or shape of the absorbent layer 44.

The topsheet 42 contacts the skin of the wearer while the training pant 20 is worn and prevents substantial contact of the absorbent layer 44 with the skin of the wearer. The topsheet 42 desirably has soft drape characteristics and good fluid penetration properties while maintaining a dry feel and clothlike aesthetics. The topsheet 42 can be treated to be hydrophilic, to more readily transport body exudates to the absorbent layer 44.

A suitable topsheet 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the topsheet 42. For example, the topsheet 42 can be composed of a meltblown or spunbond web of polyolefin fibers. The topsheet 42 can also be a bonded-carded web composed of natural and/or synthetic fibers. The topsheet 42 can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C. U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire topsheet 42 or can be selectively applied to particular sections of the topsheet 42, such as the medial section along the longitudinal centerline.

A suitable liquid permeable topsheet 42 is a nonwoven bicomponent web having a basis weight of about 1 to about 100 grams per square meter (gsm), suitably about 20 to about 40 gsm, more suitably about 27 gsm. The nonwoven bicomponent web can be a spunbond bicomponent web, or a bonded-carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the backsheet 40 and the topsheet 42 can comprise elastomeric materials, it can be desirable in some embodiments for the composite structure to be generally inelastic, where the backsheet 40, the topsheet 42 and the absorbent layer 44 comprise materials that are generally not elastomeric.

The backsheet 40 desirably comprises a material that is substantially liquid impermeable, and can be elastic, stretchable or nonstretchable. The backsheet 40 can be a single layer of liquid impermeable material, but desirably comprises a multi-layered laminate structure in which at least one of the layers is liquid impermeable. For instance, the backsheet 40 can include a liquid permeable outer layer and a liquid impermeable inner layer between the liquid permeable outer layer and the absorbent layer 44. The liquid permeable outer layer and the liquid impermeable inner layer are suitably joined together by a laminate adhesive. Suitable laminate adhesives, which can be applied continuously or intermittently as beads, a spray, parallel swirls, or the like, can be obtained from Findley Adhesives, Inc., of Wauwatosa; Wis., U.S.A., or from National Starch and Chemical Company, Bridgewater, N.J., U.S.A. The liquid permeable outer layer can be any suitable material and desirably is one that provides a generally cloth-like texture. One example of such a material is a 20 gsm (grams per square meter) spunbond polypropylene nonwoven web. The outer layer may also be made of those materials of which the liquid permeable topsheet 42 is made. While it is not a necessity for the outer layer to be liquid permeable, it is desired that it provides a relatively cloth-like texture to the wearer.

The inner layer and the outer layer can be both liquid and vapor impermeable, or can be liquid impermeable and vapor permeable. The inner layer is desirably manufactured from a thin plastic film, although other flexible liquid impermeable material may also be used. The inner layer, or the liquid impermeable outer cover when a single layer, prevents waste material from wetting articles, such as bedsheets and clothing, as well as the wearer and caregiver. A suitable liquid impermeable film for use as a liquid impermeable inner layer, or a single layer liquid impermeable outer cover, is a 0.02 millimeter polyethylene film commercially available from Huntsman Packaging of Newport News, Va., U.S.A. If the outer cover is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc. Tokyo, Japan, or an XKO-8044 polyolefin film commercially available from 3M Company, Minneapolis, Minn., U.S.A.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A swellable absorbent structure comprising:
   a swellable layer including one of a semi-circular shape and an arcuate shape, the swellable layer temporarily bonded in a compressed configuration with a water-soluble adhesive and swellable in at least one direction upon activation by at absorption of a liquid; and
   a liquid permeable cover material covering at least a portion of the swellable layer and adapted to expand upon swelling of said swellable layer;
   wherein the swellable absorbent structure forms a containment dam for fecal matter upon swelling of the swellable layer.

2. The swellable structure of claim 1, wherein the swellable layer is selected from the group consisting of SAM/fluff batt, compressed cellulose, compressed foam structure and combinations thereof.

3. The swellable absorbent structure comprising:
   a swellable layer temporarily bonded in a compressed configuration with a water-soluble adhesive and swellable in at least one direction; and
   a cover material adapted to expand upon swelling of said swellable layer;
   wherein the swellable absorbent structure forms a containment dam for fecal matter upon swelling of the swellable layer.

4. The swellable structure of claim 1, wherein the swellable layer has an initial thickness of about 0.05 inch to about 0.5 inch.

5. The swellable structure of claim 1, wherein the swellable layer has an initial thickness of about 0.1 inch to about 0.3 inch.

6. The swellable structure of claim 1, wherein the swellable layer has a swelled thickness of about 0.2 inch to about 1.5 inch.

7. The swellable structure of claim 1, wherein the swellable layer has a swelled thickness of about 0.4 inch to about 1.0 inch.

8. The swellable structure of claim 1, wherein the swellable layer swells unidirectionally.

9. The swellable structure of claim 8, wherein the swellable layer swells in a direction perpendicular to an inner surface.

10. The swellable structure of claim 1, wherein the swellable layer comprises an absorbent swellable layer.

11. The swellable structure of claim 1, wherein the cover material is pleated.

12. The swellable structure of claim 11, wherein the pleated cover material has a pleat configuration comprising one of a single z-fold pleat, a multiple accordion pleat, and a gusset pleat.

13. The swellable structure of claim 1, wherein the cover material comprises a nonwoven web.

14. The swellable structure of claim 13, wherein the nonwoven web comprises one of a carded staple fiber and a spunbond.

15. The swellable structure of claim 1, wherein the cover material comprises one of an apertured film, a foam and a woven fabric web.

16. A personal care absorbent article comprising:
    an absorbent chassis having an inner surface, the inner surface configured to contact a wearer of the personal care absorbent article; and
    a swellable structure attachable to the inner surface, the swellable structure comprising a swellable absorbent layer temporarily bonded in a compressed configuration with a water-soluble adhesive and a liquid permeable cover material covering at least a portion of the swellable absorbent layer, the cover material adapted to expand upon swelling of said swellable absorbent layer, wherein the swellable absorbent structure forms a containment dam for fecal matter upon swelling of the swellable layer.

17. The personal care absorbent article of claim 16, wherein the cover material is pleated.

18. The personal care absorbent article of claim 16, comprising a feminine hygiene product.

19. The personal care absorbent article of claim 16, comprising a diaper.

20. The personal care absorbent article of claim 16, comprising training pants.

21. The personal care absorbent article of claim 16, comprising absorbent underpants.

22. The personal care absorbent article of claim 16, comprising an adult incontinence article.

23. A swellable absorbent structure comprising:
    a swellable absorbent layer including one of a semi-circular shape and an arcuate shape, the swellable absorbent layer temporarily bonded compressed configuration with a water-soluble adhesive and having an initial thickness of about 0.1 to about 0.3 inch in a compressed state and a final thickness of about 0.4 inch to about 1.0 inch in a swelled state; and
    a pleated liquid permeable cover material covering at least a portion of the swellable absorbent layer and adapted to expand to cover the swellable absorbent layer in the swelled state;
    wherein the swellable absorbent structure swells upon activation by at absorption of a liquid and forms a containment dam for containing fecal matter.

24. The swellable structure of claim 3, wherein the swellable layer is selected from the group consisting of SAM/fluff batt, compressed cellulose, compressed foam structure and combinations thereof.

25. The swellable structure of claim 3, wherein the cover material is pleated.

* * * * *

UNITED STATES PATENT AND TRADEMARK OFFICE
CERTIFICATE OF CORRECTION

PATENT NO.   : 6,908,458 B1
DATED        : June 30, 2005
INVENTOR(S)  : Barbara O. Sauer and Laura Turner It is certified that error appears in the above-identified patent and that said Letters Patent is hereby corrected as shown below:

<u>Column 10,</u>
Line 36, should read -- absorbant layer temporarily bonded in a compressed configuration --.

Signed and Sealed this

Thirtieth Day of August, 2005

JON W. DUDAS
*Director of the United States Patent and Trademark Office*